(12) United States Patent
Zhou (10) Patent No.: US 11,737,895 B2
(45) Date of Patent: Aug. 29, 2023

(54) ACETABULAR CUP HOLDER FOR HIP JOINT

(71) Applicant: TY Medical Co., Ltd., Jiangsu (CN)

(72) Inventor: Haili Zhou, Jiangsu (CN)

(73) Assignee: TY Medical Co., Ltd., Jiangsu (CN)

( * ) Notice: Subject to any disclaimer, the term of this patent is extended or adjusted under 35 U.S.C. 154(b) by 65 days.

(21) Appl. No.: 17/243,611

(22) Filed: Apr. 29, 2021

(65) Prior Publication Data
US 2022/0151803 A1 May 19, 2022

(30) Foreign Application Priority Data
Nov. 18, 2020 (CN) .......................... 202011292860.9

(51) Int. Cl.
*A61F 2/46* (2006.01)
(52) U.S. Cl.
CPC .................................. *A61F 2/4609* (2013.01)
(58) Field of Classification Search
CPC ........................... A61F 2/46; A61F 2002/4629
See application file for complete search history.

(56) References Cited

U.S. PATENT DOCUMENTS

| | | | |
|---|---|---|---|
| 7,682,363 B2 * | 3/2010 | Burgi | A61F 2/4609 606/88 |
| 2006/0149285 A1 * | 7/2006 | Burgi | A61F 2/4609 606/99 |
| 2007/0173856 A1 * | 7/2007 | Parker | A61F 2/34 606/99 |

FOREIGN PATENT DOCUMENTS

WO   WO-2005044153 A1 *   5/2005   ........... A61F 2/4609

* cited by examiner

*Primary Examiner* — Anu Ramana
(74) *Attorney, Agent, or Firm* — Gang Yu (57) ABSTRACT

The disclosure discloses an acetabular cup holder for a hip joint, including a rubber-covered spindle. One end of the rubber-coated spindle is connected with a guide rod. A cup holding rod is arranged in the guide rod. The cup holding rod is provided with a screw thread at a position close to an opening end of the guide rod, and the screw thread extends out of the guide rod. A spring is arranged in a closed end of the guide rod. Kidney-shaped holes are formed in a side wall of a middle portion of the guide rod. A limiting pin is arranged at a position, corresponding to the kidney-shaped holes, of the cup holding rod. On one side of the kidney-shaped holes, a force releasing knob sleeves the outside of the guide rod. The limiting pin penetrates the kidney-shaped holes to be overlapped on the force releasing knob.

11 Claims, 7 Drawing Sheets

ACETABULAR CUP HOLDER FOR HIP JOINT

CROSS-REFERENCE TO RELATED APPLICATION(S)

The disclosure claims priority to Chinese Patent Application No. 202011292860.9, filed on Nov. 18, 2020 and entitled "Acetabular Cup Holder for Hip Joint", the disclosure of which is hereby incorporated by reference in its entirety.

TECHNICAL FIELD

The disclosure relates to the technical field of medical instruments, and particularly to an acetabular cup holder for a hip joint.

BACKGROUND

The hip joint is an articulation of the acetabulum and the femoral head. With the aid of the cartilage, synovial membrane, and fibrous capsule, the hip joint forms a flexible spherical joint of which the structure is like a ball embedded in a groove. Due to the structure, the hip joint has high stability to support weight of a human body.

The hip joint is needed as a support point to support various activities of the human body. If the hip joint is subjected to function deficits, such as diseases of the hip joint: degenerative hip osteoarthritis, rheumatoid hip osteoarthritis, traumatic hip osteoarthritis, congenital hip dysplasia, and the like due to factors such as high degeneration, rheumatoid symptoms, traumas or diseases, people's normal life will be inevitably greatly affected. In such case, medical personnel are required to perform hip replacement. The hip replacement involves trimming the acetabulum and the femoral head of the affected hip joint and then replacing them with artificial joints.

A total artificial hip joint is a very important pivot component for the hip replacement, which may substantially include an acetabular cup embedded in bone tissue of the pelvic acetabulum of the human body, and an artificial hip joint ball head extending to be provided with an artificial femur. The artificial hip joint ball head is fitted in a fitting position of the acetabular cup. Through a wear-resistant liner between the acetabular cup and the artificial hip joint ball head, the artificial hip joint ball head may be pivoted in the acetabular cup, to simulate movement manners of the human femur in the acetabulum.

How to accurately place the acetabular cup into the bone tissue of the pelvic acetabulum of the human body is an important issue for medical personnel. Generally speaking, in an art known to inventors, the medical personnel may hold a rod-shaped acetabular cup holder for a hip joint with hands, and one end of the holder is provided with the acetabular cup in a threaded locking manner. During surgery, the medical personnel insert an acetabular cup implanter into an appropriate position of the patient's bone tissue of the pelvic acetabulum for fitting. After the acetabular cup is fitted at the fitting position in the human body, the acetabular cup holder for the hip joint is rotated to remove the acetabular cup. There is also an art that may prevent the acetabular cup from being taken out of the human body or being moved due to the threaded locking when the acetabular cup holder for the hip joint is removed. However, the acetabular cup holder known to inventors still has many defects.

I. The acetabular cup holder for the hip joint clamps the acetabular cup by means of both the threaded locking and an external cylinder pressure. However, during clamping, the medical personnel need to hold the acetabular cup holder for the hip joint with one hand while rotating a knob with the other hand, thereby achieving the clamping of the acetabular cup by operations with both hands. Additional medical personnel are needed to take the acetabular cup, which is troublesome in operation. In removing of the acetabular cup holder for the hip joint, both hands are needed to operate in a narrow operating space, which causes a difficulty in use.

II. For the acetabular cup holder for the hip joint, in order to prevent the acetabular cup from being taken out of the human body or from being moved, a positioning hole such as a square hole is disposed in the acetabular cup. However, the acetabular cup has many specifications, particularly when the acetabular cup has a thin wall or a small specification, additional holes cannot be formed in the acetabular cup. Forcible opening may damage mechanical properties of the acetabular cup. Moreover, most of the acetabular cups in the market do not have positioning holes. Therefore, this structure has a narrow application range.

III. The acetabular cup holder for the hip joint, having a complicated structure and many parts, is not easy to clean and disinfect, and is easy to cause infection when used again.

Some embodiments of the disclosure provide an acetabular cup holder for a hip joint for solving the above problems.

SUMMARY

Some embodiments of the disclosure provide an acetabular cup holder for a hip joint, intended to solve a problem mentioned in Background.

To solve the above technical problems, some embodiments of the disclosure provide the following technical solution: an acetabular cup holder for a hip joint includes a rubber-coated spindle; a first end of the rubber-coated spindle is connected with a guide rod that is a hollow structure; a first end of the guide rod close to the rubber-coated spindle is closed, and a second end, away from the rubber-coated spindle is open; a cup holding rod is arranged in the guide rod; the cup holding rod is provided with a thread at a position close to the open end of the guide rod; the thread extends out of the guide rod; a spring is arranged in a close end of the guide rod; a kidney-shaped hole is formed in a side wall of a middle portion of the guide rod, particularly two kidney-shaped holes are correspondingly formed in the side wall of the guide rod and communicate the inside and the outside of the guide rod; a limiting pin is arranged at a position, corresponding to the kidney-shaped holes, of the cup holding rod; the limiting pin passes through and is fastened to the cup holding rod; on one side of the kidney-shaped holes, a force releasing knob sleeves the outside of the guide rod; the limiting pin passes through the kidney-shaped holes to be overlapped on the force releasing knob; and the limiting pin always provides a pressure to the force releasing knob under the action of the spring.

In clamping of an acetabular cup, the rubber-coated spindle is held with one hand, and the acetabular cup is held with the other hand; the rubber-coated spindle is rotated to drive the guide rod to rotate; meanwhile, the limiting pin drives the cup holding rod in the guide rod to rotate, to further drive the screw thread to be in threaded connection with a threaded hole in the acetabular cup, so as to clamp the acetabular cup. After the threaded connection, an inner wall of the acetabular cup is in contact with one end of the guide rod. Due to constant relative position of the guide rod and the cup holding rod, an interaction force is formed between the acetabular cup and the guide rod. The interaction force may further clamp the acetabular cup, threaded deadlock caused by clamping with the screw thread individually is avoided, and during clamping, the acetabular cup holder for the hip joint is operated with one hand only to achieve clamping of the acetabular cup.

After the acetabular cup is clamped to a fitting position in the human body, the acetabular cup holder for the hip joint is required to be removed. In such case, the force releasing knob is moved so that the pressure of the limiting pin to the force releasing knob is released. The limiting pin drives the cup holding rod, the relative position of the cup holding rod and the guide rod is slightly changed. That is, under the action of the spring, the cup holding rod slightly moves to the screw thread, the interaction force between the acetabular cup and the guide rod disappears. Further, by mutually rotating the rubber-coated spindle, the screw thread is easily screwed off the threaded hole in the acetabular cup, thereby preventing the situation that the screw thread drives the acetabular cup to rotate in the human body due to threaded deadlock. In addition, in a process of removing the acetabular cup holder for the hip joint, the interaction force from the guide rod to the acetabular cup is released before the screw thread is screwed off, there is no need to position the guide rod in advance, that is, there is no need to provide a square hole and the like based on the threaded hole in the acetabular cup, and thus, the structure has broad applicability.

In an exemplary embodiment, the force releasing knob is configured to rotate around a circumferential direction of the guide rod, and a groove is arranged at one side of the force releasing knob close to the limiting pin. When the force releasing knob is rotated, a distal end of the limiting pin located outside the guide rod is configured to match with the groove. When the acetabular cup holder is required to be removed, the force releasing knob is rotated to cause the limiting pin to extend into the groove; the cup holding rod is driven to slightly move under the action of the spring, the interaction force between the acetabular cup and the guide rod disappears, and thus force releasing is completed.

In an exemplary embodiment, a plurality of through holes are passing through lateral sides and the entire width of the force releasing knob. When the acetabular cup holder and the acetabular cup are in over-tightening threaded locking, force releasing is achieved by inserting a round bar into one through hole to turn the force releasing knob.

In an exemplary embodiment, a reverse knocking block also sleeves the outside of the guide rod. The reverse knocking block is used for reverse adjustment, and is fixed to the guide rod. A curve slot is arranged at a first end of the reverse knocking block close to the force releasing knob. A guide post is arranged at one end of the force releasing knob close to the reverse knocking block; the guide post is fixed onto the force releasing knob, and inserted into the curve slot. A reset spring is arranged in the curve slot. A first end of the reset spring is abutted against the corresponding guide post, and a second end thereof is abutted in an inside surface of the curve slot. When being rotated, the force releasing knob may drive the guide post to compress the reset spring. After the acetabular cup holder is removed, the reset spring bounce to drive the guide post to reset along the curve slot, to further drive the force releasing knob to reversely rotate, so that the limiting pin and the groove are staggered from each other, and the pressure to the force releasing knob from the limiting pin is formed again. Therefore, automatic resetting of the acetabular cup holder for the hip joint is completed, which saves time when it is used again.

In an exemplary embodiment, the groove is an arc groove, and a first end of the limiting pin is a convex surface, the first end of the limiting pin is capable of extending into the groove. The arc groove and the convex surface are used to assist the reset spring, to complete automatic resetting of the acetabular cup holder for the hip joint.

In an exemplary embodiment, the curve slots are stepped kidney-shaped slots, which are used to prevent the force releasing knob from excessive rotation to drive the guide posts to excessively compress the reset springs, thereby achieving functions of limiting and protecting the reset springs.

In an exemplary embodiment, a length, in the guide rod, of the screw thread is L. Since different doctors hold the acetabular cup with different strengths, when the screw thread and the threaded hole are locked with an appropriate strength, the screw thread and the threaded hole may be in deadlock if the rubber-coated spindle continues to be rotated, which is unconducive to subsequent operations. Since the screw thread is located at a length a in the guide rod, the guide rod is stressed when the rubber-coated spindle continues to be rotated, thereby preventing the screw thread from deadlock, and further protecting the screw thread against damages.

In an exemplary embodiment, the length of the screw thread is 2 mm.

In an exemplary embodiment, a plurality of through slots are formed in the side wall of the guide rod, and communicate the inside and the outside of the guide rod, which makes the post-operative cleaning more thorough and prevents intraoperative infection. The through slots are provided with circular arc chamfers at the outer side of the guide rod, which may make the guide rod smoother and may not cause damages to other tissue of the human body.

In an exemplary embodiment, a knocking block is arranged at a second end of the rubber-coated spindle. The knocking block is designed to be plane, to prevent the acetabular cup holder for the hip joint from being driven to roll by a knocking force.

Compared with the related art, some embodiments of the disclosure have the following beneficial effects.

1. According to the acetabular cup holder for the hip joint disclosed in some embodiments of the disclosure, a user only needs to hold the acetabular cup with one hand, and hold and rotate the rubber-coated spindle with the other hand, so as to complete clamping of the acetabular cup. In removing of the acetabular cup holder for the hip joint, the user only needs to release the pressure of the force releasing knob, and then rotate the rubber-coated spindle. Compared with the acetabular cup holder for the hip joint known to inventors, the acetabular cup holder for the hip joint is convenient to use and easy to operate, saves manpower, and is suitable to be operated within a narrow operation space.

2. According to the acetabular cup holder for the hip joint disclosed in some embodiments of the disclosure, the acetabular cup is effectively clamped by a clamping force from the threaded connection between the screw thread and the threaded hole, and the interaction force formed between the acetabular cup and the guide rod. The two clamping forces restrict each other, threaded deadlock is avoided in clamping of the acetabular cup holder for the hip joint, and the acetabular cup is prevented from being taken out of the human body or being moved in a subsequent removing process of the acetabular cup.

3. According to the acetabular cup holder for the hip joint disclosed in some embodiments of the disclosure, in clamping of the acetabular cup, there is no need to position the screw thread of the acetabular cup, and no need to provide the positioning hole such as the square hole in the acetabular cup; thus, the acetabular cup holder for the hip joint may adapt to most acetabular cups and thin-wall acetabular cups applied in the market, and has wide application range and high practicability.

4. According to the acetabular cup holder for the hip joint disclosed in some embodiments of the disclosure, when the screw thread and the threaded hole are locked with an appropriate strength, the screw thread and the threaded hole may be in deadlock if the rubber-coated spindle continues to be rotated, which is unconducive to subsequent operations. Since the screw thread is located at the length of 2 mm in the guide rod, the guide rod is stressed when the rubber-coated spindle continues to be rotated, thereby preventing the screw thread from deadlock, and further protecting the screw thread against damages.

5. According to the acetabular cup holder for the hip joint disclosed in some embodiments of the disclosure, after the acetabular cup holder for the hip joint is removed, the reset springs bounce to drive the guide posts to reset along the curve slots respectively, to further drive the force releasing knob to reversely rotate, so that the limiting pin and the groove are staggered from each other, and the pressure to the force releasing knob from the limiting pin is formed again. Therefore, automatic resetting of the acetabular cup holder for the hip joint is achieved, which saves time when it is used again.

6. According to the acetabular cup holder for the hip joint disclosed in some embodiments of the disclosure, the through slots are formed in the side wall of the guide rod, and communicate the inside and the outside of the guide rod, which makes the post-operative cleaning more thorough and prevents intraoperative infection.

7. According to the acetabular cup holder for the hip joint disclosed in some embodiments of the disclosure, the through holes are formed in the lateral side of the force releasing knob. When the acetabular cup holder for the hip joint and the acetabular cup are in over-tightening threaded locking, force releasing is achieved by inserting the round bar into one through hole to turn the force releasing knob.

BRIEF DESCRIPTION OF THE DRAWINGS

The accompany drawings are used to provide further understanding of the disclosure, and form a part of the description. The accompany drawings and embodiments of the disclosure are adopted to explain the disclosure, and do not form limits to the disclosure. In the drawings.

Description of reference numerals in the drawings is as follows:

1. rubber-coated spindle; 2. guide rod; 3. cup holding rod; 4. screw thread; 5. spring; 6. kidney-shaped hole; 7. limiting pin; 8. force releasing knob; 9. groove; 10. reverse knocking block; 11. curve slot; 12. guide post; 13. reset spring; 14. through slot; 15. knocking block; and 16. through hole.

DETAILED DESCRIPTION OF THE EMBODIMENTS

The technical solutions in the embodiments of the disclosure will be clearly and completely described below in combination with the drawings in the embodiments of the disclosure. Obviously, the described embodiments are not all embodiments but part of embodiments of the disclosure. All other embodiments obtained by those of ordinary skilled in the art on the basis of the embodiments in the disclosure without creative work shall fall within the scope of protection of the disclosure. Embodiments: some embodiments of the disclosure provide the technical solution. As shown in FIG. 1 to FIG. 4, an acetabular cup holder for a hip joint includes a rubber-coated spindle 1, a guide rod 2 and a cup holding rod 3. A first end of the rubber-coated spindle 1 is connected to the guide rod 2 that is a hollow structure. A first end of the guide rod 2 facing the rubber-coated spindle 1 is closed, and a second end, away from the rubber-coated spindle 1 is open. The cup holding rod 3 is arranged in the guide rod 2. A screw thread 4 is arranged in a first end of the rod holding rod 3 facing the open end of the guide rod 2. An outer surface of the guide rod 2 is threaded. A spring 5 is arranged in a close end of the guide rod 2. A kidney-shaped hole 6 is formed in a side wall of the guide rod 2, in some embodiments, two kidney-shaped holes 6 are correspondingly formed in the side wall of the guide rod 2 and communicate the inside and the outside of the guide rod 2. A limiting pin 7 is arranged at the second end of the cup holding rod 3, the limiting pin 7 is inserted in the kidney-shaped holes 6. The limiting pin 7 passes through and is fixed to the guide rod 2. A force releasing knob 8 is located around the guide rod 2. The limiting pin 7 passes through the kidney-shaped holes 6 and is abutted against the force releasing knob 8. The limiting pin 7 always provides a pressure to the force releasing knob 8 under the action of the spring 5.

In clamping of an acetabular cup, the rubber-coated spindle 1 is held with one hand, and the acetabular cup is held with the other hand; the rubber-coated spindle 1 is rotated to drive the guide rod 2 to rotate; meanwhile, the limiting pin 7 drives the cup holding rod 3 in the guide rod 2 to rotate, to drive the screw thread 4 to be in threaded connection with a threaded hole in the acetabular cup, so as to clamp the acetabular cup. After the threaded connection, an inner wall of the acetabular cup contacts with one end of the guide rod 2. Due to constant relative position of the guide rod 2 and the cup holding rod 3, an interaction force is formed between the acetabular cup and the guide rod 2. The interaction force further clamps the acetabular cup, threaded deadlock caused by clamping with the screw thread individually is avoided, and during clamping, the acetabular cup holder for the hip joint is operated with one hand only to complete the clamping of the acetabular cup.

After the acetabular cup is clamped to a fitting position in the human body, the acetabular cup holder for the hip joint is required to be removed. In such case, the force releasing knob 8 is moved, so that the pressure of the limiting pin 7 to the force releasing knob 8 is released. The limiting pin 7 may cause a slight change of the relative position of the cup holding rod 3 and the guide rod 2. That is, under the action of the spring 5, the cup holding rod 3 slightly moves to the screw thread 4, the interaction force between the acetabular cup and the guide rod 2 disappears. Further, by mutually rotating the rubber-coated spindle 1, the screw thread 4 is easily screwed off the threaded hole in the acetabular cup, thereby preventing the situation that the screw thread 4 drives the acetabular cup to rotate in the human body due to threaded deadlock. In a process of removing the acetabular cup holder for the hip joint, the interaction force from the guide rod 2 to the acetabular cup is released before the screw thread 4 is screwed off, there is no need to position the guide rod 2 in advance, that is, there is no need to provide a square hole and the like based on the threaded hole of the acetabular cup, and thus, the structure has broad applicability.

Figure 3:
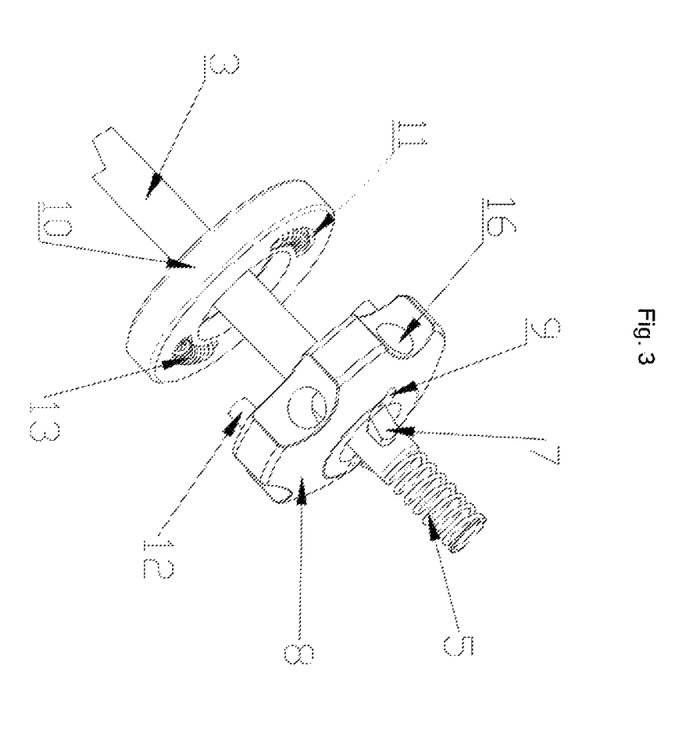
FIG. 3 illustrates a perspective view of a force releasing knob, a reverse knocking block, and the like in the acetabular cup holder for the hip joint of an embodiment of the disclosure.
Figure 4:
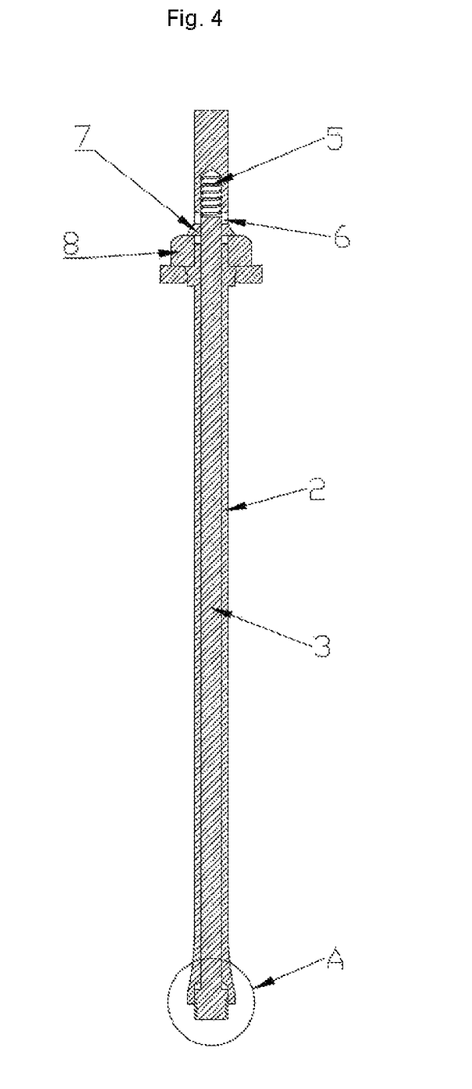
FIG. 4 illustrates a sectional view of an acetabular cup holder for a hip joint of an embodiment of the disclosure.

As shown in FIG. 3, the force releasing knob 8 is configured to circumferentially rotate around the guide rod 2, and a groove 9 is arranged at a side of the force releasing knob 8 close to the limiting pin 7. When the force releasing knob 8 is rotated, a distal end of the limiting pin 7 located outside the guide rod 2 is configured to be received in the groove 9. When the acetabular cup holder for the hip joint is required to be removed, the force releasing knob 8 is rotated to cause the limiting pin 7 to be received in the groove 9; the cup holding rod 3 is driven to slightly move under the action of the spring 5, the interaction force between the acetabular cup and the guide rod 2 disappears, and thus force releasing is completed.

As shown in FIG. 3, a plurality of through holes 16 pass through lateral sides and the entire width of the force releasing knob 8. When the acetabular cup holder for the hip joint and the acetabular cup are in over-tightening threaded locking, force releasing is achieved by inserting a round bar into one through hole 16 to turn the force releasing knob 8.

As shown in FIG. 3, in some embodiments, a reverse knocking block 10 is received over the outside of the guide rod 2. The reverse knocking block 10 is used for reverse adjustment, and is fixed with the guide rod 2. Curved slots 11 are arranged at a first end of the reverse knocking block 10 in a top surface of the reverse knocking block facing the force releasing knob 8. Guide posts 12 are arranged at a first end of the force releasing knob 8 facing the reverse knocking block 10, and the guide posts 12 are fixed to the force releasing knob 8, and are respectively inserted into the curved slots 11. Reset springs 13 are respectively arranged in the curved slots 11. A first end of each reset spring 13 is abutted against the corresponding guide post 12, and a second end thereof is abutted in an inside surface of the reverse knocking block 10 defining the corresponding curved slot 11. When being rotated, the force releasing knob 8 may drive the guide posts 12 to compress the reset springs 13. After the acetabular cup holder for the hip joint is removed, the reset springs 13 bounce to drive the guide posts 12 to reset along the curved slots 11 respectively, to further drive the force releasing knob 8 to reversely rotate, so that the limiting pin 7 and the groove 9 are staggered from each other, and the pressure to the force releasing knob 8 from the limiting pin 7 is formed again. Therefore, automatic resetting of the acetabular cup holder for the hip joint is achieved, which saves time when it is used again.

As shown in FIG. 3, in some embodiments, the groove 9 is an arc groove. A first end of the limiting pin is a convex surface, the first end of the limiting pin is capable of extending into the groove 9. The arc groove and the convex surface are used to assist the reset springs 13, thereby completing automatic resetting of the acetabular cup holder for the hip joint.

In some embodiments of the disclosure, each of the curved slots 11 is a stepped kidney-shaped groove, which is used to prevent the force releasing knob 8 from excessive rotation to drive the guide posts 12 to excessively compress the reset springs 13, thereby achieving functions of limiting and protecting the reset springs 13.

Figure 6:
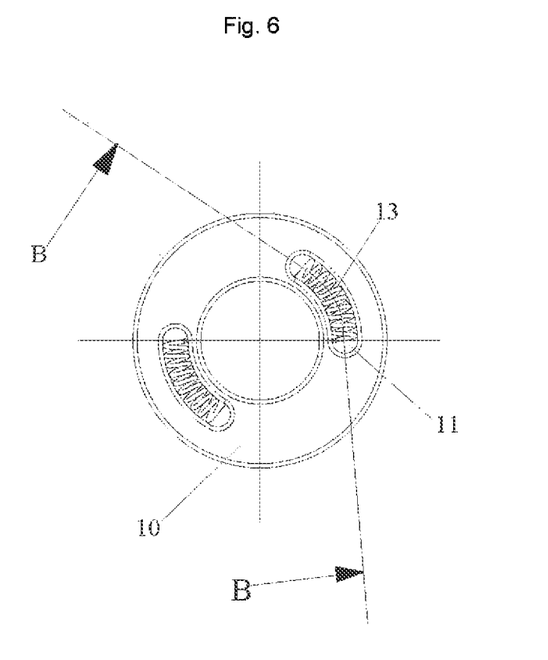
FIG. 6 illustrates a top view of a reverse knocking block of the acetabular cup holder for the hip joint in FIG. 1.
Figure 7:
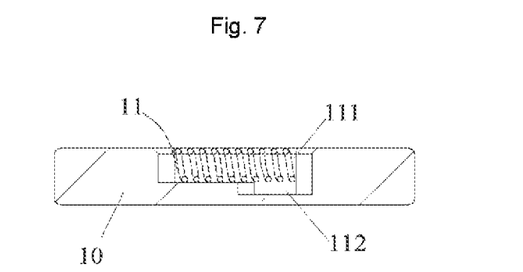
FIG. 7 illustrates a B-B sectional view of FIG. 6.

FIG. 6 and FIG. 7 illustrate a structural view of a curved slot, as shown in FIG. 7, the curved slot 11 includes a first slot 111 and a second slot 112 in communication with the first slot 111. Wherein, the reset spring 13 is located in the first slot 111, the guide post 12 cooperates with the second slot 112. The second slot 112 is configured to limit the movement stroke of the guide post 112, so as to limit a rotation angle of the force releasing knob 8.

Figure 5:
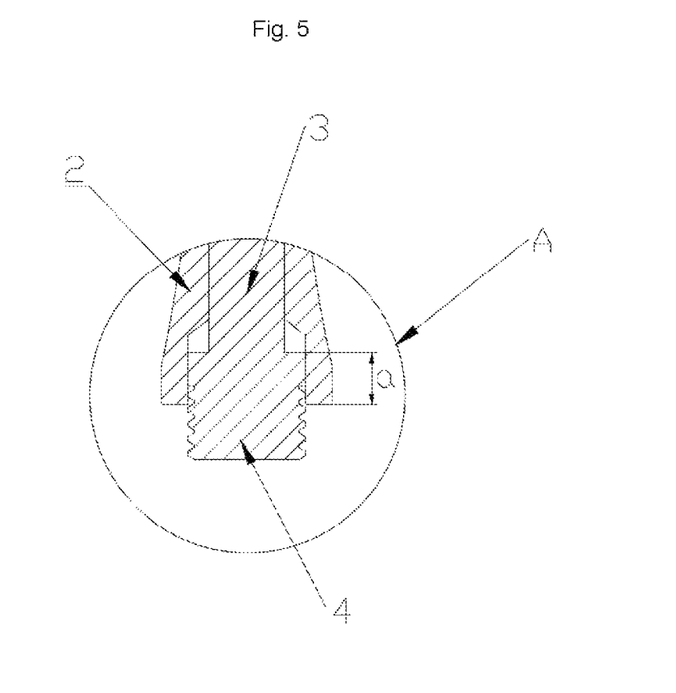
FIG. 5 illustrates detailed view of A of an embodiment of the disclosure.

As shown in FIG. 5, in some embodiments, a length of the screw thread 4 is L=2 mm. Since different doctors hold the acetabular cup with different strengths, when the screw thread 4 and the threaded hole are locked with an appropriate strength, the screw thread 4 and the threaded hole is in deadlock if the rubber-coated spindle 1 continues to be rotated, which is unconducive to subsequent operations. Since the screw thread 4 is located at the length of 2 mm in the guide rod 2, the guide rod 2 is stressed when the rubber-coated spindle 1 continues to be rotated, thereby preventing the screw thread 4 from deadlock, and further protecting the screw thread against damages.

Figure 2:
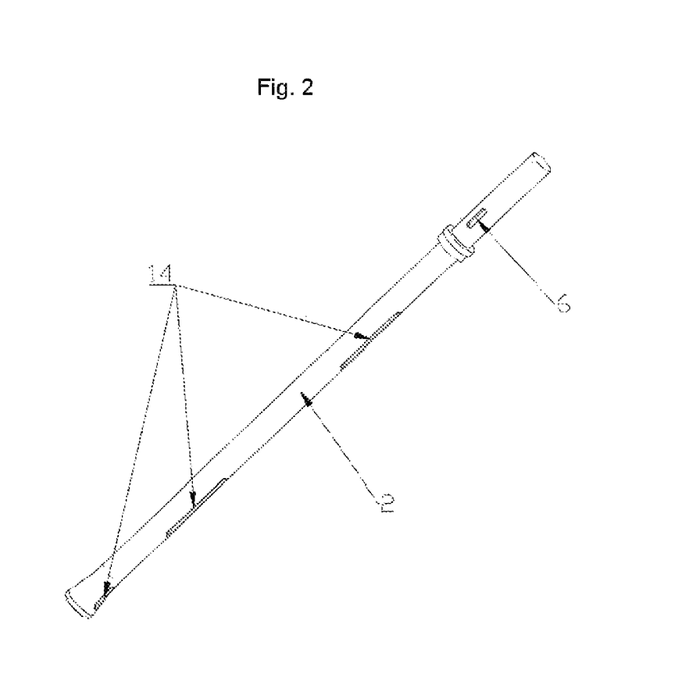
FIG. 2 illustrates a perspective view of a guide rod in the acetabular cup holder for the hip joint of an embodiment of the disclosure.

As shown in FIG. 2, in some embodiments, a plurality of through slots 14 are formed in the side wall of the guide rod. The through slots 14 communicate the inside and the outside of the guide rod 2, which makes the post-operative cleaning more thorough and prevent intraoperative infection. A circular arc chamfer is provided in an outside surface of the guide rod 2 defining the plurality of through slots 14, which make the guide rod smoother and may not cause damages to other tissue of the human body.

Figure 1:
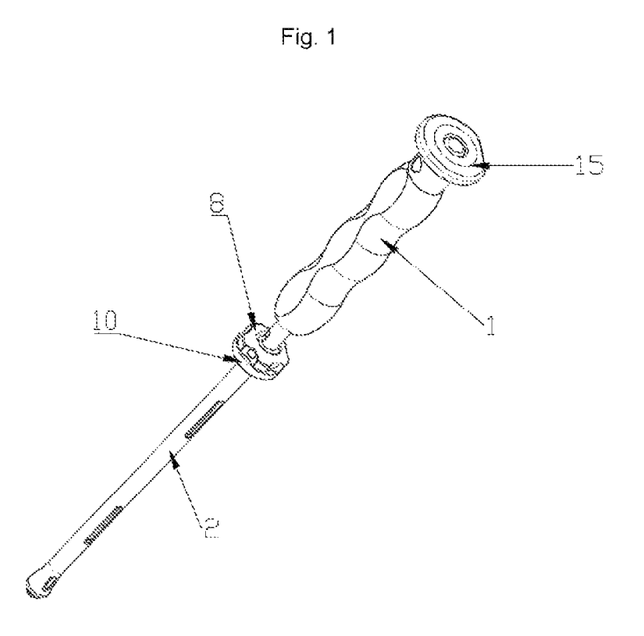
FIG. 1 illustrates a perspective view of an acetabular cup holder for a hip joint of an embodiment of the disclosure.

As shown in FIG. 1, in some embodiments, a knocking block 15 is arranged at a second end of the rubber-coated spindle 1. The knocking block 15 is designed to be plane, to prevent the acetabular cup holder for the hip joint from being driven to roll by a knocking force.

Figure 8:
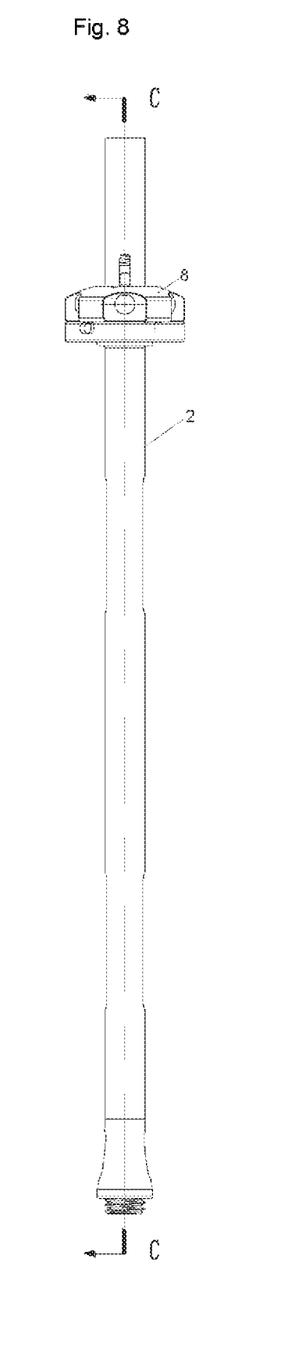
FIG. 8 illustrates a front view of an acetabular cup holder for a hip joint of an embodiment of the disclosure.
Figure 9:
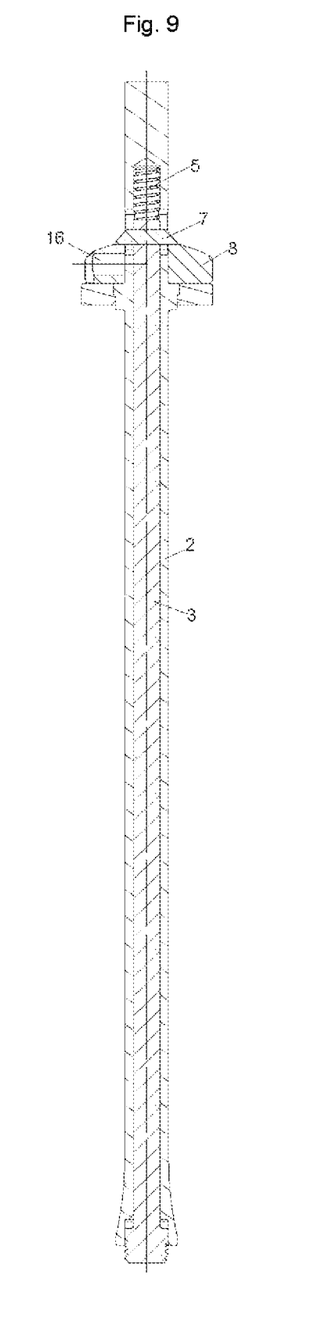
FIG. 9 illustrates a C-C sectional view of FIG. 8.

FIG. 8 illustrates a front view of an acetabular cup holder for a hip joint of an embodiment of the disclosure;

FIG. 9 illustrates a C-C sectional view of FIG. 8. In the FIG. 9, the limiting pin 7 is fixed and arranged at the second end of the cup holding rod 3, and the limiting pin 7 is inserted in the kidney-shaped hole 6 of the guide rod 2.

Working principles of some embodiments of the disclosure: in clamping of the acetabular cup, the rubber-coated spindle 1 is held with one hand, and the acetabular cup is held with the other hand; the rubber-coated spindle 1 is rotated to drive the guide rod 2 to rotate; meanwhile, the limiting pin 7 drives the cup holding rod 3 in the guide rod 2 to rotate, to drive the screw thread 4 to be in threaded connection with a threaded hole in the acetabular cup, so as to clamp the acetabular cup. After the threaded connection, an inner wall of the acetabular cup is in contact with one end of the guide rod 2. Due to unchanged relative position of the guide rod 2 and the cup holding rod 3, an interaction force is formed between the acetabular cup and the guide rod 2.

The interaction force further clamps the acetabular cup, threaded deadlock caused by clamping with the thread individually is avoided.

After the acetabular cup is clamped to the fitting position in the human body, the acetabular cup holder for the hip joint is required to be removed. In such case, the force releasing knob 8 is moved so that the pressure of the limiting pin 7 to the force releasing knob 8 is released. The limiting pin 7 causes a slight change of the relative position of the cup holding rod 3 and the guide rod 2. That is, under the action of the spring 5, the cup holding rod 3 slightly moves to the screw thread 4, the interaction force between the acetabular cup and the guide rod 2 disappears. Further, by mutually rotating the rubber-coated spindle 1, the screw thread 4 is easily screwed off the threaded hole in the acetabular cup, thereby preventing the situation that the screw thread 4 drives the acetabular cup to rotate in the human body due to threaded deadlock. In a process of removing the acetabular cup holder for the hip joint, the counter force from the guide rod 2 to the acetabular cup is released before the screw thread 4 is screwed off, there is no need to position the guide rod 2 in advance, that is, there is no need to provide the square hole and the like based on the threaded hole in the acetabular cup, and thus, the structure has broad applicability.

It is to be noted that relative terms such as "first" and "second" are only adopted to distinguish one entity or operation from another entity or operation, and are not necessarily required or implied that there is any such actual relationship or order between these entities or operations. Terms "comprise", "include", or any other variations thereof are intended to cover non-exclusive inclusions, so that processes, methods, articles or devices containing a series of elements not only contain these elements, but also contain other elements which are not clearly listed, or further contain elements which are inherent to these processes, methods, articles or devices.

It is to be noted at last: the above descriptions are only some embodiments of the disclosure and are not used to limit the disclosure. Although the disclosure has been described in detail with reference to the foregoing embodiments, for those skilled in the art, they can still modify the technical solutions described in the foregoing embodiments, or equivalently replace some of the technical features. Any modifications, equivalent replacements, improvements and the like within the spirit and principle of the disclosure shall fall within the scope of protection of the disclosure.

What is claimed is:

1. An acetabular cup holder for a hip joint, comprising a rubber-covered spindle, a guide rod, a cup holding rod and a spring, wherein a first end of the rubber-coated spindle is connected with the guide rod; the cup holding rod is arranged in the guide rod; a screw thread is arranged at a first end of the cup holding rod, and the spring is arranged at a second end of the cup holding rod; an outer surface of the guide rod is threaded; a kidney-shaped hole is formed in a side wall of the guide rod; a limiting pin is arranged at the second end of the cup holding rod, the limiting pin is inserted in the kidney-shaped hole; a force releasing knob is located around the guide rod; and the limiting pin passes through the kidney-shaped hole and is abutted against the force releasing knob.

2. The acetabular cup holder for the hip joint according to claim 1, wherein the force releasing knob is configured to circumferentially rotate around the guide rod, a groove is arranged on a side of the force releasing knob close to the limiting pin, and when the force releasing knob is rotated, a distal end of the limiting pin located outside the guide rod is configured to be received in the groove.

3. The acetabular cup holder for the hip joint according to claim 2, wherein a reverse knocking block is received over the outside of the guide rod and is used for reverse adjustment; a curved slot is arranged at a first end of the reverse knocking block in a top surface of the reverse knocking block facing the force releasing knob; a guide post is arranged at a first end of the force releasing knob facing the reverse knocking block; the guide post is inserted into the curved slot; a reset spring is arranged in the curved slot; a first end of the reset spring is abutted against the guide post, and a second end of the reset spring is abutted in an inside surface of the reverse knocking block defining the curved slot.

4. The acetabular cup holder for the hip joint according to claim 3, wherein the curved slot is a stepped kidney-shaped slot, wherein the curved slot comprises a first slot and a second slot in communication with the first slot, the reset spring is located in the first slot, the guide post cooperates with the second slot, the second slot is configured to limit the movement stroke of the guide post.

5. The acetabular cup holder for the hip joint according to claim 3, wherein the groove is an arc groove, and one end of the limiting pin is a convex surface, the end of the limiting pin is capable of extending into the arc groove.

6. The acetabular cup holder for the hip joint according to claim 2, wherein the groove is an arc groove, and a first end of the limiting pin is a convex surface, the first end of the limiting pin is capable of extending into the groove.

7. The acetabular cup holder for the hip joint according to claim 1, wherein a plurality of through holes pass through lateral sides and the entire width of the force releasing knob.

8. The acetabular cup holder for the hip joint according to claim 1, wherein a length of the screw thread is L.

9. The acetabular cup holder for the hip joint according to claim 8, wherein L=2 mm.

10. The acetabular cup holder for the hip joint according to claim 1, wherein a plurality of through slots are formed in the side wall of the guide rod, and a circular arc chamfer is provided in an outside surface of the guide rod defining the plurality of through slots.

11. The acetabular cup holder for the hip joint according to claim 1, wherein a knocking block is arranged at a second end of the rubber-coated spindle.

\* \* \* \* \*